US00PP20856P2

(12) United States Plant Patent

Kanaya

(10) Patent No.: US PP20,856 P2
(45) Date of Patent: Mar. 16, 2010

(54) *CALIBRACHOA* PLANT NAMED 'SUNCALSIFOPI'

(50) Latin Name: *Calibrachoa sp.*
Varietal Denomination: Suncalsifopi

(75) Inventor: Takeshi Kanaya, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 12/313,692

(22) Filed: Nov. 21, 2008

(51) Int. Cl.
*A01H 5/00* (2006.01)

(52) U.S. Cl. ..... Plt./413

(58) Field of Classification Search ..... Plt./263, Plt./413

See application file for complete search history.

*Primary Examiner*—Susan B McCormick Ewoldt
(74) *Attorney, Agent, or Firm*—C. A. Whealy

(57) ABSTRACT

A new and distinct cultivar of *Calibrachoa* plant named 'Suncalsifopi', characterized by its compact and mounding plant habit; vigorous growth habit; freely branching and flowering plant habit; early and long flowering period; medium-sized pale pink-colored flowers; and good garden performance.

1 Drawing Sheet

Botanical designation: *Calibrachoa* sp.
Cultivar denomination: 'SUNCALSIFOPI'.

BACKGROUND OF THE INVENTION

The present invention relates to a new and distinct cultivar of *Calibrachoa* plant, botanically known as *Calibrachoa* sp. and hereinafter referred to by the name 'Suncalsifopi'.

The new *Calibrachoa* plant is a product of a planned breeding program conducted by the Inventor in Higashiomi, Shiga, Japan. The objective of the breeding program is to develop new compact, mounding and freely-branching *Calibrachoa* cultivars with attractive and unique flower coloration.

The new *Calibrachoa* plant originated from a cross-pollination conducted by the Inventor in Higashiormi, Shiga, Japan in April, 2004 of a proprietary selection of *Calibrachoa* sp. identified as code number LBS81, not patented, as the female, or seed, parent with a proprietary selection of *Calibrachoa* sp. identified as code number LBS65, not patented, as the male, or pollen, parent. The new *Calibrachoa* was discovered and selected by the Inventor as a single flowering plant from within the progeny of the stated cross-pollination in a controlled greenhouse environment in Higashiomi, Shiga, Japan in September, 2005.

Asexual reproduction of the new *Calibrachoa* plant by vegetative cuttings in a controlled greenhouse environment in Higashiomi, Shiga, Japan since October, 2005, has shown that the unique features of this new *Calibrachoa* plant are stable and reproduced true to type in successive generations.

SUMMARY OF THE INVENTION

Plants of the new *Calibrachoa* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Suncalsifopi'. These characteristics in combination distinguish 'Suncalsifopi' as a new and distinct cultivar of *Calibrachoa:*

1. Compact and mounding plant habit.
2. Vigorous growth habit.

3. Freely branching and flowering plant habit.
4. Early and long flowering period.
5. Medium-sized pale pink-colored flowers.
6. Good garden performance.

Plants of the new *Calibrachoa* can be compared to plants of the female parent selection. Plants of the new *Calibrachoa* differ from plants of the female parent selection in the following characteristics:

1. Plants of the new *Calibrachoa* are taller than plants of the female parent selection.
2. Plants of the new *Calibrachoa* and the female parent selection differ in flower color as plants of the female parent selection have red purple-colored flowers.

Plants of the new *Calibrachoa* can be compared to plants of the male parent selection. Plants of the new *Calibrachoa* differ from plants of the male parent selection in the following characteristics:

1. Plants of the new *Calibrachoa* are taller than plants of the male parent selection.
2. Plants of the new *Calibrachoa* and the male parent selection differ in flower color as plants of the male parent selection have red purple-colored flowers.

Plants of the new *Calibrachoa* can also be compared to plants of 'Sunbelkos', disclosed in U.S. Plant Pat. No. 15,094. In side-by-side comparisons conducted in Higashiomi, Shiga, Japan, plants of the new *Calibrachoa* and 'Sunbelkos' differed primarily in the following characteristics:

1. Plants of the new *Calibrachoa* were more compact than plants of 'Sunbelkos'.
2. Plants of the new *Calibrachoa* were more mounding than plants of 'Sunbelkos'.
3. Plants of the new *Calibrachoa* were more freely branching than plants of 'Sunbelkos'.
4. Plants of the new *Calibrachoa* had shorter leaves than plants of 'Sunbelkos'.
5. Plants of the new *Calibrachoa* were more freely flowering than plants of 'Sunbelkos'.
6. Plants of the new *Calibrachoa* flowered earlier than plants of 'Sunbelkos'.
7. Plants of the new *Calibrachoa* had larger flowers than plants of 'Sunbelkos'.

8. Plants of the new *Calibrachoa* and 'Sunbelkos' differed in flower color as plants of 'Sunbelkos' had light red purple-colored flowers.

BRIEF DESCRIPTION OF THE PHOTOGRAPHS

The accompanying colored photographs illustrate the overall appearance of the new *Calibrachoa,* showing the colors as true as it is reasonably possible to obtain in colored reproductions of this type. Colors in the photographs may differ slightly from the color values cited in the detailed botanical description which accurately describe the colors of the new *Calibrachoa.*

The photograph at the top of the sheet comprises a side perspective view of a typical flowering plant of 'Suncalsifopi' grown in a container.

The photograph at the bottom of the sheet is a close-up view of a typical flower of 'Suncalsifopi'.

DETAILED BOTANICAL DESCRIPTION

The aforementioned photographs and following observations, measurements and values describe plants grown in Higashiomi, Shiga, Japan, under commercial practice during the late spring in an outdoor nursery. During the production of the plants, day temperatures averaged 23° C. and night temperatures averaged 13° C. Plants had been growing for four and five months when the description and photographs, respectively, were taken. In the following description, color references are made to The Royal Horticultural Society Colour Chart, 2001 Edition, except where general terms of ordinary dictionary significance are used.

Botanical classification: *Calibrachoa* sp. 'Suncalsifopi'.

Parentage:

*Female, or seed, parent.*—Proprietary selection of *Calibrachoa* sp. identified as code number LBS81, not patented.

*Male, or pollen, parent.*—Proprietary selection of *Calibrachoa* sp. identified as code number LBS65, not patented.

Propagation:

*Type.*—By vegetative cuttings.

*Time to initiate roots.*—About one week at 15° C. to 20° C.

*Time to produce a rooted young plant.*—About three weeks at 15° C. to 20° C.

*Root description.*—Fibrous; white in color.

*Rooting habit.*—Freely branching.

Plant description:

*Plant and growth habit.*—Compact and mounding plant habit. Freely branching habit with numerous lateral branches developing per plant; pinching is not required, but will enhance lateral branch development; vigorous growth habit.

*Plant height.*—About 18.9 cm.

*Plant diameter.*—About 42 cm.

Lateral branch description:

*Length.*—About 24 cm.

*Diameter.*—About 1.8 mm.

*Internode length.*—About 1.3 cm.

*Strength.*—Strong.

*Aspect.*—Upright to outward.

*Texture.*—Pubescent.

*Color.*—Close to 144B.

Foliage description:

*Arrangement.*—Alternate, simple.

*Length.*—About 3.2 cm.

*Width.*—About 1.2 cm.

*Shape.*—Narrowly elliptic.

*Apex.*—Broadly acute to obtuse.

*Base.*—Cuneate.

*Margin.*—Entire.

*Texture, upper and lower surfaces.*—Pubescent.

*Venation pattern.*—Pinnate; reticulate.

*Color.*—Developing leaves, upper surface: Close to 144B. Developing leaves, lower surface: Close to 146C. Fully expanded leaves, upper surface: Close to 137B; venation, close to 145A. Fully expanded leaves, lower surface: Close to 138C; venation, close to 145A.

*Petiole.*—Length: About 3.7 mm. Diameter: About 0.9 mm. Texture, upper and lower surfaces: Sparsely pubescent. Color, upper and lower surfaces: Close to 145A.

Flower description:

*Flower arrangement and habit.*—Single salverform flowers arising from upper leaf axils. Freely flowering habit with usually about 57 open flowers per plant at one time. Flowers face upright or outwardly.

*Fragrance.*—Not detected.

*Natural flowering season.*—Early flowering habit; plants of the new *Calibrachoa* initiate and develop flowers about three weeks after planting. Long flowering period; flowering commences naturally during the spring and plants flower continuously throughout the summer until late autumn in Japan.

*Flower longevity.*—Individual flowers last about seven to ten days on the plant; flowers not persistent.

*Flower diameter.*—About 3.5 cm.

*Flower length (depth).*—About 3.3 cm.

*Throat diameter.*—About 9.8 mm.

*Tube length.*—About 2 cm.

*Tube diameter.*—About 1.9 mm.

*Flower bud.*—Shape: Cylindrical. Length: About 2.3 cm. Diameter: About 9.1 mm. Color: Close to 76A.

*Corolla.*—Arrangement: Five petals fused at the base and opening into a flared trumpet. Petal length from throat: About 1.2 cm. Petal width: About 1.6 cm. Petal shape: Spatulate. Petal apex: Truncate. Petal margin: Entire. Petal texture, upper and lower surfaces: Smooth, glabrous. Throat texture: Smooth, glabrous. Tube texture: Pubescent. Color: Petal, when opening, upper surface: Close to 75A; towards the throat, close to 85B. Petal, when opening, lower surface: Close to 75B. Petal, fully opened, upper surface: Close to 75A; towards the throat, close to 85C; venation, close to 77A. Petal, fully opened, lower surface: Close to 75B. Throat: Close to 13B; venation, close to 13B. Tube: Close to 163D; venation, close to 163D.

*Calyx.*—Arrangement: One star-shaped calyx tube with five sepals fused at the base. Sepal length: About 8 mm to 13 mm. Sepal width: About 4 mm. Sepal shape: Lanceolate. Sepal apex: Acute. Sepal margin: Entire. Sepal texture, upper and lower surfaces: Pubescent. Color, immature and mature, upper surface: Close to 144A. Color, immature and mature, lower surface: Close to 144A.

*Peduncles.*—Length: About 1.2 cm. Diameter: About 0.8 mm. Angle: Upright to outward. Strength: Strong. Texture: Pubescent. Color: Close to 144B.

*Reproductive organs.*—Stamens: Quantity/arrangement: Five per flower. Stamen length: About 9 mm. Anther shape: Ellipsoidal. Anther size: About 1.4 mm by 1.4 mm. Anther color: Close to 8D. Pollen amount: Moderate. Pollen color: Close to 8D. Pistils: Quantity: One per flower. Pistil length: About 8.4 mm. Style color: Close to 144D. Stigma shape: Trans versely ellipsoidal. Stigma color: Close to 144C. Ovary color: Close to 144B. Seed/fruit: Seed and fruit development have not been observed on plants of the new *Calibrachoa*.

Garden performance: Plants of the new *Calibrachoa* have been observed to have good garden performance and to tolerate wind, rain and temperatures ranging from about 5° C. to about 35° C.

Pathogen/pest resistance: Plants of the new *Calibrachoa* have not been observed to be resistant to pests and pathogens common to *Calibrachoa*.

It is claimed:

1. A new and distinct *Calibrachoa* plant named 'Suncalsifopi' as illustrated and described.

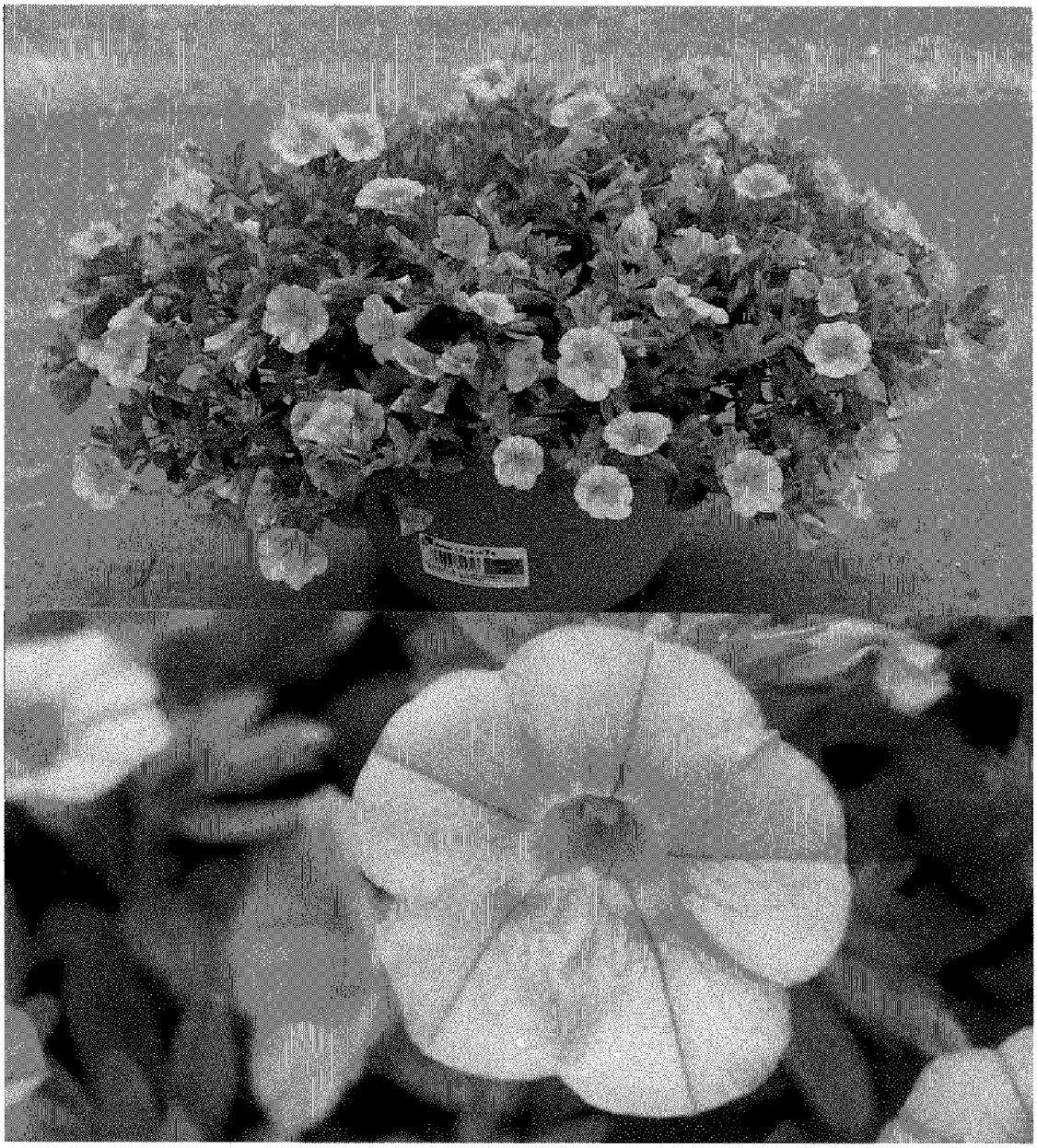

* * * * *